(12) United States Patent
Wendland et al.

(10) Patent No.: US 10,653,844 B2
(45) Date of Patent: May 19, 2020

(54) AUTO-INJECTOR

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 177 days.

(21) Appl. No.: 15/778,349

(22) PCT Filed: Nov. 21, 2016

(86) PCT No.: PCT/EP2016/078281
§ 371 (c)(1),
(2) Date: May 23, 2018

(87) PCT Pub. No.: WO2017/089289
PCT Pub. Date: Jun. 1, 2017

(65) Prior Publication Data
US 2018/0326159 A1    Nov. 15, 2018

(30) Foreign Application Priority Data
Nov. 27, 2015   (EP) ..................................... 15196666

(51) Int. Cl.
*A61M 5/315*   (2006.01)
*A61M 5/20*    (2006.01)
(52) U.S. Cl.
CPC ...... *A61M 5/31511* (2013.01); *A61M 5/2033* (2013.01); *A61M 2005/206* (2013.01);
(Continued)

(58) Field of Classification Search
CPC ........ A61M 5/178; A61M 5/20; A61M 5/315; A61M 5/31; A61M 5/31576;
(Continued)

(56) References Cited

U.S. PATENT DOCUMENTS

| | | | |
|---|---|---|---|
| 2011/0184351 A1* | 7/2011 | Holmqvist | A61M 5/2033 604/187 |
| 2013/0218093 A1* | 8/2013 | Markussen | A61M 5/001 604/198 |

FOREIGN PATENT DOCUMENTS

| | | |
|---|---|---|
| CN | 204610647 | 9/2015 |
| WO | WO 2010/037759 | 4/2010 |

(Continued)

OTHER PUBLICATIONS

PCT International Preliminary Report on Patentability in International Appln. No. PCT/EP2016/078281, dated May 29, 2018, 8 pages.

(Continued)

*Primary Examiner* — Jason E Flick
(74) *Attorney, Agent, or Firm* — Fish & Richardson P.C.

(57) ABSTRACT

An auto-injector for delivering a liquid medicament includes a housing arranged to contain a syringe with a piston for sealing the syringe and displacing the medicament, the housing having a proximal end and a distal end and a telescopic plunger unit arranged between the piston and the proximal end of the housing, the telescopic plunger unit comprising a telescopic frame and a spring element surrounding a plunger element. The plunger element is fixed to a base of the telescopic plunger unit and the spring element is held in an initial compressed state by a compressive force exerted by the base of the telescopic plunger unit. When the spring element is released, a tapering profile of the telescopic frame is configured to provide varying friction with extension such that resistance to telescopic extension (Continued)

decreases as spring force provided by the spring element decreases with increasing extension of the telescopic plunger unit.

12 Claims, 7 Drawing Sheets

(52) U.S. Cl.
CPC ............ *A61M 2005/2026* (2013.01); *A61M 2005/2073* (2013.01); *A61M 2005/31518* (2013.01)

(58) Field of Classification Search
CPC ...... A61M 5/31565; A61M 2005/2026; A61M 2005/206; A61M 2005/2073; A61M 2005/31518; A61M 5/2033; A61M 5/31511

USPC ........................................................ 604/135
See application file for complete search history.

(56) References Cited

FOREIGN PATENT DOCUMENTS

| WO | WO 2012/025639 | 3/2012 | | |
|----|----|----|----|----|
| WO | WO 2012/031627 | 3/2012 | | |
| WO | WO-2012031627 A1 * | 3/2012 | .......... | A61M 5/2033 |

OTHER PUBLICATIONS

PCT International Search Report and Written Opinion in International Appln. No. PCT/EP2016/078281, dated Feb. 13, 2017, 12 pages.

* cited by examiner

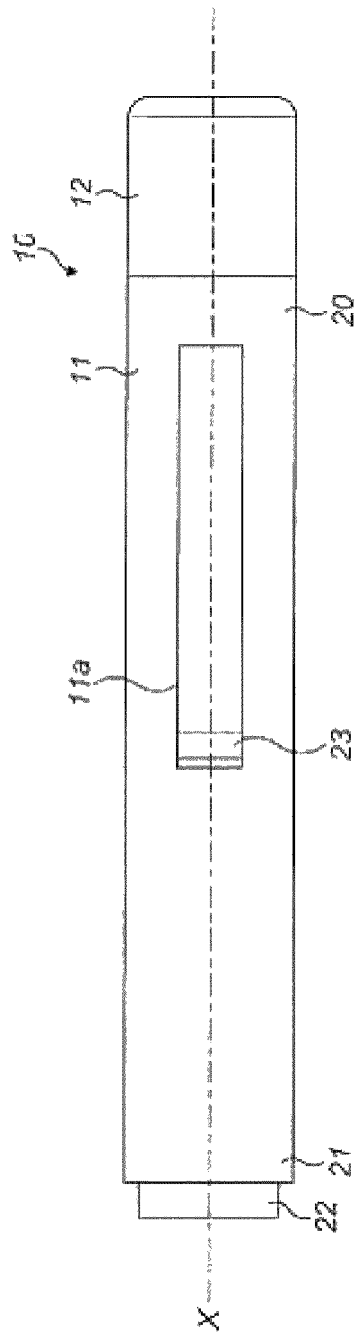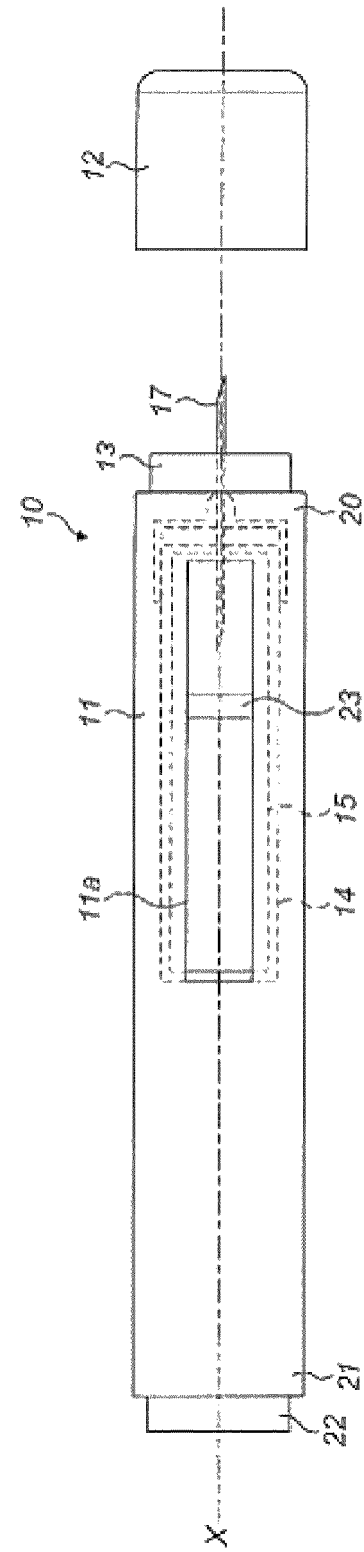
FIG. 1A
FIG. 1B

AUTO-INJECTOR

CROSS REFERENCE TO RELATED APPLICATIONS

The present application is the national stage entry of International Patent Application No. PCT/EP2016/078281, filed on Nov. 21, 2016, and claims priority to Application No. EP 15196666.0, filed in on Nov. 27, 2015, the disclosures of which are expressly incorporated herein in entirety by reference thereto.

TECHNICAL FIELD

The present disclosure relates to an auto-injector for delivering a liquid medicament to a user.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger. There are numerous disadvantages inherent with user of a manual device. For example, if the user stops depressing the plunger, less than a full dose of the liquid medicament may be delivered. Furthermore, the force required to depress the plunger may be problematic for elderly users or those with dexterity problems, which may lead to trembling or shaking when aligning or the injection and/or while administering the dose of the liquid medicament. In addition, the extension of the button or plunger of manual devices may be too great. Thus it can be inconvenient for the user to reach a fully extended button.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

In some auto-injectors the energy to deliver the fluid is provided by a spring. However, in some auto-injectors the pushing force exerted by the spring for pushing the liquid medicament out of the syringe of the auto-injector may vary in an undesirable way throughout the delivery of a dose. This may lead to delivery of medicament at a non-constant force and thus may have a high impact on the user when the injection is triggered.

SUMMARY

According to an aspect of the present disclosure, there is provided an auto-injector for delivering a liquid medicament comprising: a housing arranged to contain a syringe with a piston for sealing the syringe and displacing the medicament, the housing having a proximal end and a distal end intended to be applied against an injection site; and a telescopic plunger unit arranged between the piston and the proximal end of the housing, the telescopic plunger unit comprising a telescopic frame and a spring element surrounding a plunger element, wherein the plunger element is fixed to a base of the telescopic plunger unit and the spring element is held in an initial compressed state by a compressive force exerted by the base of the telescopic plunger unit; wherein when the spring element is released, a tapering profile of the telescopic frame is configured to provide varying friction with extension such that resistance to telescopic extension decreases as spring force provided by the spring element decreases with increasing extension of the telescopic plunger unit, and wherein a combination of the decreasing spring force provided by the spring element and the decreasing resistance to telescopic extension may provide a substantially constant resultant driving force exerted on the base of the telescopic plunger unit, such that a substantially constant pushing force is exerted on the piston when the spring element is released.

Since the driving force provided by the spring element is a spring force which decreases as the spring is released and begins to decompress, and the tapering profile of the telescopic frame provides varying friction with extension such that resistance to telescopic extension decreases as the spring force decreases, the resultant force exerted on the piston of the syringe can be relatively constant as it is being pushed towards the distal end of the housing for displacing the liquid medicament contained within the syringe, or at least is more constant that would be the case without the telescopic frame. This alleviates the problem of undesirable varying pushing force on the piston which may lead to high impact on the user when the injection is triggered.

The auto-injector may further comprise a locking mechanism arranged at the proximal end of the housing, the locking mechanism being configured such that when disengaged, the spring element releases and exerts a driving force on the base of the telescopic plunger unit, thereby forwarding load of the spring element to the plunger element and extending the telescopic plunger unit, pushing the piston towards the distal end of the housing to displace the medicament.

The substantially constant resultant driving force may have a force profile gradient of at least 80% less than that of a gradient of the decreasing spring force.

The telescopic frame may comprise a plurality of telescopic plunger parts, and each of the plurality of telescopic plunger parts may have a conical frustum shape. The conical frustum shape of the telescopic plunger parts allows friction at a point of contact between the telescopic plunger parts to decrease during extension of the telescopic plunger unit. This is due to the increasing inner diameter of the telescopic plunger parts towards one end.

The plurality of telescopic plunger parts may comprise an outermost telescopic plunger part, and the outermost telescopic plunger part is fixedly attached to the proximal end of the housing.

The auto-injector may further comprise a locking mechanism arranged at the proximal end of the housing, the locking mechanism being configured such that when disengaged, the spring element releases and exerts a driving force on the base of the telescopic plunger unit, thereby forwarding load of the spring element to the plunger element and extending the telescopic plunger unit, pushing the piston towards the distal end of the housing to displace the medicament.

The locking mechanism may comprise a first locking element provided at the plunger element and a second locking element, the first and second locking elements being configured to be releasably engaged with each other. Such an arrangement allows the plunger element to be easily released from an initial state upon disengagement of the locking mechanism.

The first locking element may be a groove provided at the plunger element, and the second locking element may be a movable projection, wherein when the projection is in a first position it is engaged with the groove so as to hold the spring element in the initial compressed state, and when the projection is in a second position it is disengaged from the groove such that the spring element is released. By using this mechanical arrangement, the plunger element can be released by simply moving the projection. This eliminates the need for an extending button for pushing a plunger and therefore prevents problems associated with users attempting to reach a fully extended button.

The first locking element may be a slot provided at the plunger element, and the second locking element may be a hook provided at a rotatable cap at the proximal end of the housing, wherein when the hook is in a first orientation it is engaged with the slot so as to hold the spring element in the initial compressed state, and when the hook is in a second orientation it is disengaged from the slot such that the spring element is released.

The second orientation may be achieved by rotating the rotatable cap from the first orientation.

Knurls may be provided on an outer edge of the rotatable cap.

A medicament may be included in the syringe.

According to another aspect of the present disclosure, there is provided a method of maintaining a substantially constant resultant driving force in an auto-injector having a telescopic plunger unit and a spring element, wherein a tapering profile of a telescopic frame of the telescopic plunger unit is configured to provide varying friction with extension such that resistance to telescopic extension decreases as spring force provided by the spring element decreases with increasing extension of the telescopic plunger unit, and a combination of the decreasing spring force provided by the spring element and the decreasing resistance to telescopic extension provides the substantially constant resultant driving force exerted on a base of the telescopic plunger unit.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which:

FIGS. 1A and 1B are side-on views of an auto-injector device according to an embodiment of the present disclosure;

Reference will now be made in detail to the embodiments, examples of which are illustrated in the accompanying drawings, wherein like reference numerals refer to like elements throughout.

DETAILED DESCRIPTION

Figure 2:
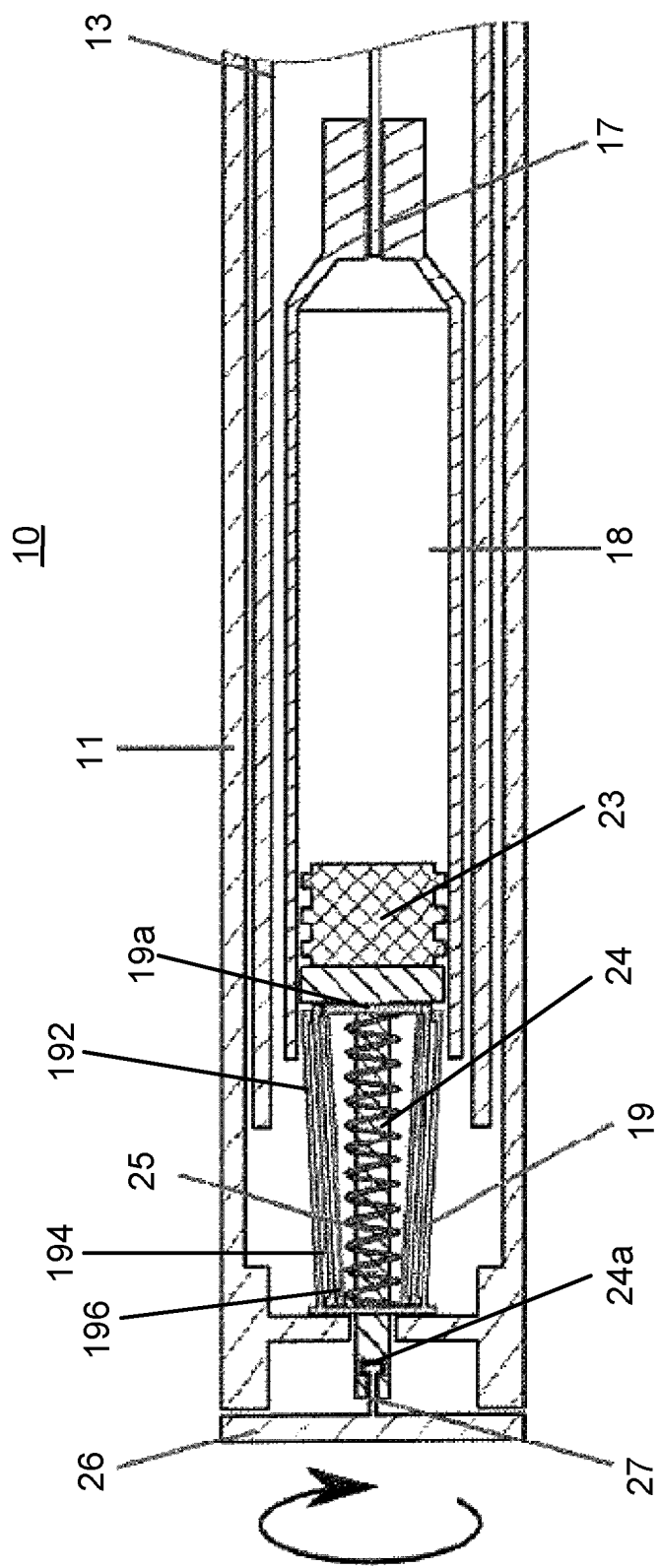
FIG. 2 is a cross-sectional view of an auto-injector in an initial state, according to a first embodiment of the present disclosure.

An auto-injector with a plunger arrangement is provided. The plunger arrangement includes a telescopic plunger unit between the piston of a syringe and a proximal end of a housing of the auto-injector. The telescopic plunger unit includes a telescopic frame having a tapering profile and a spring element surrounding a plunger element, and the plunger element is fixed to a base of the telescopic plunger unit. In an initial state, the spring element is held in a compressed state by a compressive force exerted by the base of the telescopic plunger unit, which in turn is locked in place by a locking mechanism which comprises a hook at a rotatable cap and a slot at the plunger element.

When the hook is disengaged from the slot, the spring element is released (i.e. begins to decompress) and exerts a driving force on the base of the telescopic plunger unit to push the piston of the syringe for displacing liquid medicament contained in the syringe. The telescopic frame is configured to provide varying friction with extension such that resistance to telescopic extension decreases as spring force provided by the spring element decreases with increasing extension of the telescopic plunger unit. This alleviates the problem of undesirable varying pushing force on the piston which may lead to high impact on the user when the injection is triggered.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required. FIG. 2 is a cross-sectional view of an auto-injector device 10 in an initial state, according to a first embodiment.

FIG. 2 shows an auto-injector device 10 comprising a housing 11. A syringe 18 with a hollow injection needle 17 is contained within the housing 11. The syringe 18 contains liquid medicament which is to be delivered to a patient during injection. The hollow injection needle 17 is covered with a retractable sleeve 13 which is arranged on an inner surface of the housing 11 and near a distal end of the housing 11, i.e. the direction pointing towards the patient during injection.

The syringe 18 comprises a piston, stopper or bung 23 for sealing the syringe 18 and displacing the liquid medicament, specifically towards the distal end of the housing through the hollow injection needle 17.

A telescopic plunger unit 19 is arranged between the piston 23 and the proximal end of the housing 11. The telescopic plunger unit 19 includes a telescopic frame, which comprises a plurality of telescopic plunger parts 192, 194, 196. In the present embodiment, each of the plurality of telescopic plunger parts has a conical frustum shape which provides the telescopic frame with a tapering profile. Moreover, each of the plurality of telescopic plunger parts 192, 194, 196 has a different lower base diameter, the lower base diameter being the diameter of the lower base of the conical frustum shape of the telescopic plunger part.

In the present embodiment, as illustrated in FIG. 2, the telescopic frame comprises three telescopic plunger parts, i.e. the first telescopic plunger part 192, the second telescopic plunger part 194, and the third telescopic plunger part 196.

The first telescopic plunger part 192 is the outermost telescopic plunger part and has a lower base diameter D1. In this embodiment, the first telescopic plunger part 192 is fixedly attached to a proximal end of the housing 11. The second telescopic plunger part 194 is the middle telescopic plunger part, sandwiched between the first telescopic plunger part 192 and the third telescopic plunger part 196, and has a lower base diameter D2. The third telescopic plunger part 196 is the innermost telescopic plunger part and has a lower base diameter D3. In the present embodiment, the lower base diameters of the telescopic plunger parts have the relationship: D1>D2>D3. The third telescopic plunger part, i.e. the innermost telescopic plunger part, comprises a base end which forms the base 19a of the telescopic plunger unit 19.

In the present embodiment, the telescopic frame of the telescopic plunger unit is made of a compressible material, such that friction is provided throughout the extension of the telescopic plunger unit 19 under a driving force. In particular, in this embodiment the telescopic frame is made of a polymer, e.g. PVC. The interaction and movement of the telescopic plunger parts 192, 194, 196 will be explained in further detail with respect to FIGS. 3 to 5.

The telescopic plunger unit 19 in the initial state is fully retracted, i.e. the first telescopic part 192 housing the second telescopic plunger part 194, and the second telescopic plunger part 194 housing the third telescopic plunger part 196, as shown in FIG. 2.

The telescopic plunger unit 19 also comprises a spring element 25 and a plunger element 24. The spring element 25 in the present embodiment surrounds the plunger element 24 and is held in a compressed state by a compressive force exerted by the base 19a of the telescopic plunger unit 19. In this embodiment, the spring element 25 is fixed within the telescopic plunger unit 25 by being attached both at the top and the base of the telescopic plunger unit 19.

A locking mechanism is provided so as to lock the plunger element 24 and the base of the telescopic plunger unit 19 in place in an initial state, so as to hold the spring element 25 in the compressed state. The locking mechanism comprises a first locking element 24a and a second locking element 27. In the present embodiment, the first locking element is a slot 24a arranged at a first end of the plunger element 24, and the second locking element is a hook 27 provided at a rotatable cap 26. The rotatable cap 26 is arranged at the proximal end of the housing 11.

The plunger element 24 in the present embodiment is a plunger rod that extends along the length of the telescopic plunger unit 19 when the telescopic plunger unit 19 is in a fully retracted state. A second end of the plunger element 24 is fixed to the base 19a of the telescopic plunger unit 19, i.e. the base end of the third telescopic plunger part. The second end of the plunger element 24 is opposite of the first end at which the slot 24a is formed, and the second end of the plunger element 24 is closer to the distal end of the housing 11.

FIG. 2 illustrates when the hook 27 is in a first orientation, where it is engaged with the slot 24a so as to hold the spring element in the initial compressed state. In the initial state, the spring element 25 is held in a compressed state by the compressive force exerted by the base 19a of the telescopic plunger unit 19. The telescopic plunger unit 19 is in turn held in place in the fully retracted state by the T-shaped hook 27 at the rotatable cap 26 that is releasably engaged with the slot 24a of the plunger element 24. A second orientation of the hook 27 can be achieved by rotating the rotatable cap 26.

As will be explained with respect to FIGS. 3 and 4, when the locking mechanism, i.e. the hook 27 and the slot 24a, is disengaged, the spring element 25 releases (i.e. begins to decompress) and exerts a driving force on the base 19a of the telescopic plunger unit 19. The telescopic plunger unit 19 extends under this driving force as illustrated in FIGS. 3 and 4.

Figure 3:
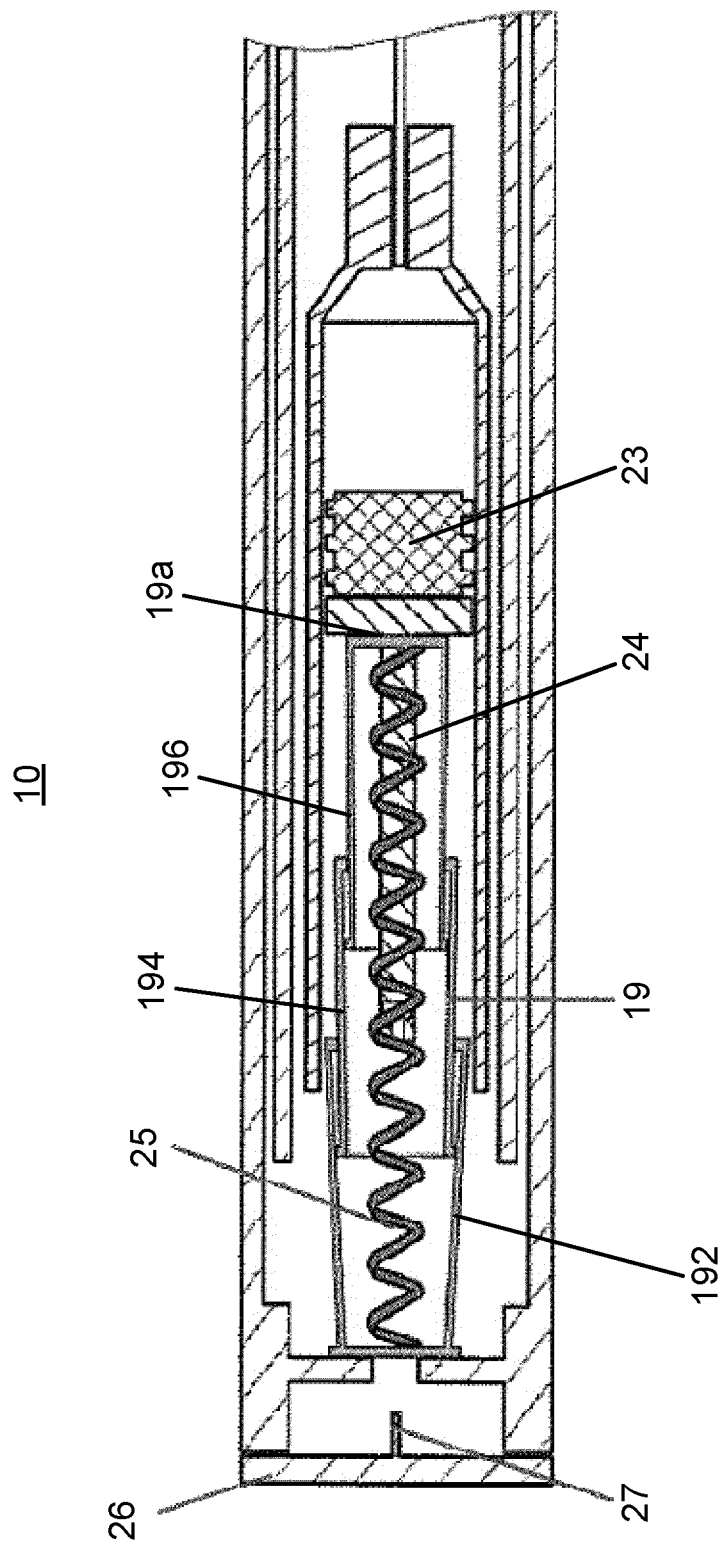
FIG. 3 is a cross-sectional view of the auto-injector in an intermediate state, according to the first embodiment of the present disclosure.
Figure 4:
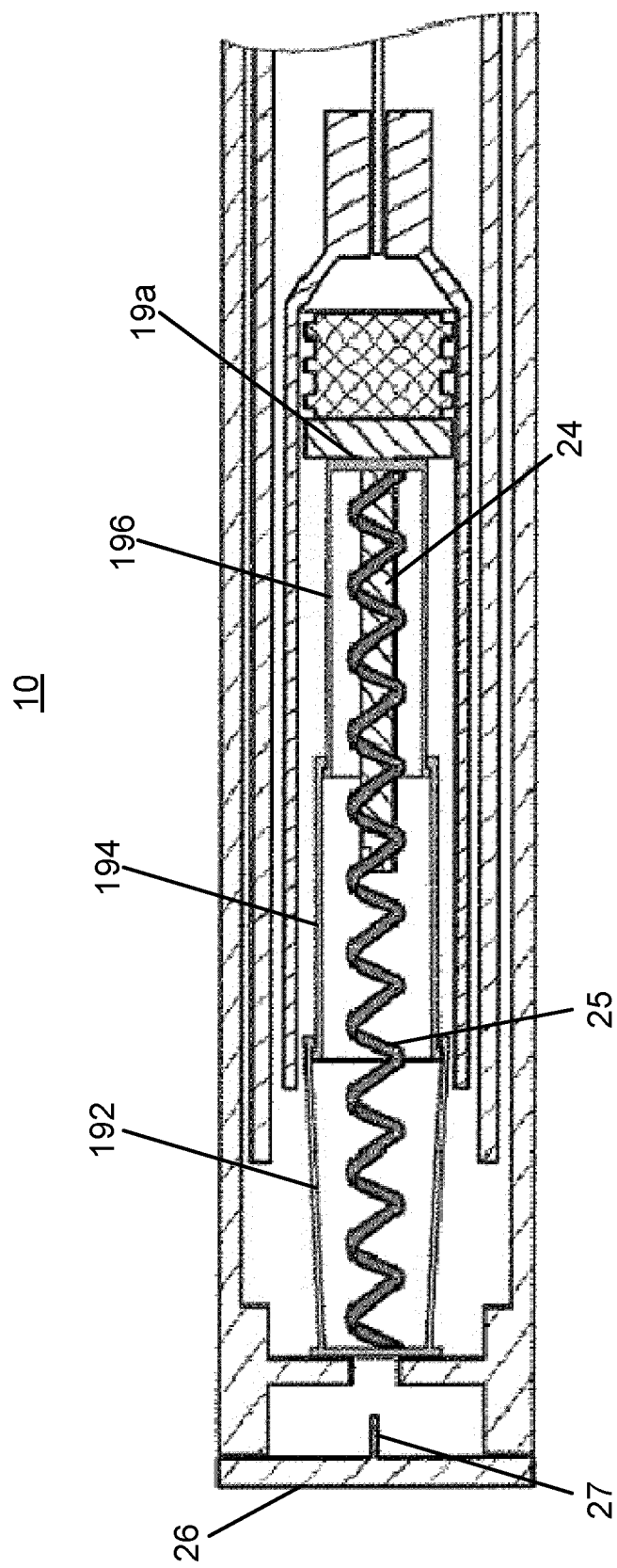
FIG. 4 is a cross-sectional view of the auto-injector in a final state, according to the first embodiment of the present disclosure.

FIG. 3 is a cross-sectional view of the auto-injector device 10 in an intermediate state, according to the first embodiment. FIG. 3 in particular illustrates an intermediate state between the initial state of the auto-injector device 10 in which the telescopic plunger unit 19 is fully retracted and the final state of the auto-injector device 10 in which the telescopic plunger unit 19 is fully extended.

As explained above, the locking mechanism, i.e. the hook 27 and the slot 24a, can be disengaged by rotating the rotatable cap 26 such that the hook is in a second orientation. In the present embodiment, the second orientation of the hook 27 is achieved by rotating the rotatable cap 26 90° from the first orientation. This is shown in FIG. 3 where the T-shaped hook 27 has been rotated by 90°.

In order to facilitate rotation, knurls or the like (not shown in the drawing) are provided on an outer edge of the rotatable cap 26 in the present embodiment so that friction between the user's fingers and the outer edge is increased. Moreover, the rotatable cap 26 in the present embodiment is made of rubber, so as to allow the cap 26 to be easily gripped. In addition, a protrusion is provided at the rotatable cap 12 (not illustrated in the drawing) for allowing a user to grip and rotate the cap 26.

In the intermediate state of the auto-injector device 10, the telescopic plunger unit 19 is partially extended. As shown in FIG. 3, a top circumference (i.e. an end of the telescopic plunger part with a smaller diameter) of the second telescopic plunger part 194 is in contact with an inner surface of the first telescopic plunger part 192. Similarly, a top circumference of the third telescopic plunger part 196 is in contact with an inner surface of the second telescopic plunger part 194. The points of contact between the telescopic plunger parts 192, 194, 196 are points of friction as the telescopic plunger unit 19 extends. The force profile of the friction force will be explained in further detail with respect to FIG. 7.

FIG. 4 is a cross-sectional view of the auto-injector device 10 in a final state, according to the first embodiment. In the final state of the auto-injector device 10, the telescopic plunger unit 19 is fully extended, and the piston 23 is pushed towards the distal end of the housing 11 in order to discharge the liquid medicament contained within the syringe 18.

It is preferred that when the telescopic plunger unit 19 is in the fully extended state that the piston 23 reaches the distal end of the syringe 18 and discharges all the liquid medicament contained within the syringe. The telescopic plunger unit 19 in the fully extended state has a length corresponding to the distance between the proximal end of the housing 11 and the piston 23, when the piston 23 is at the distal end of the syringe 18.

A sequence of the operation of the auto-injector device 10 according to the first embodiment is as follows:

In order to trigger an injection, the auto-injector device 10 is pressed against an injection site, e.g. a patient's skin. A user, e.g. the patient or a caregiver, grabs the auto-injector device 10 with their whole hand and pushes the distal end of the auto-injector device 10 against the injection site.

When pushed against the injection site, the retractable sleeve 13 of the auto-injector device 10 retracts into the housing 11 to expose the hollow injection needle 17, ready for injection. After the needle 17 has been inserted into the injection site, the rotatable cap 12 is rotated by 90°, such that the T-shaped hook 27 of the rotatable cap 12 is disengaged from the slot 24a of the plunger element 24. Upon the release of the hook 27 from the slot 24a, the spring element 25 releases (i.e. begins to decompress) and exerts a driving force on the base 19a of the telescopic plunger unit 19. This driving force pushes the piston 23 towards the distal end of the syringe 18 in order to deliver the liquid medicament contained in the syringe 18 to the patient.

Figure 5:
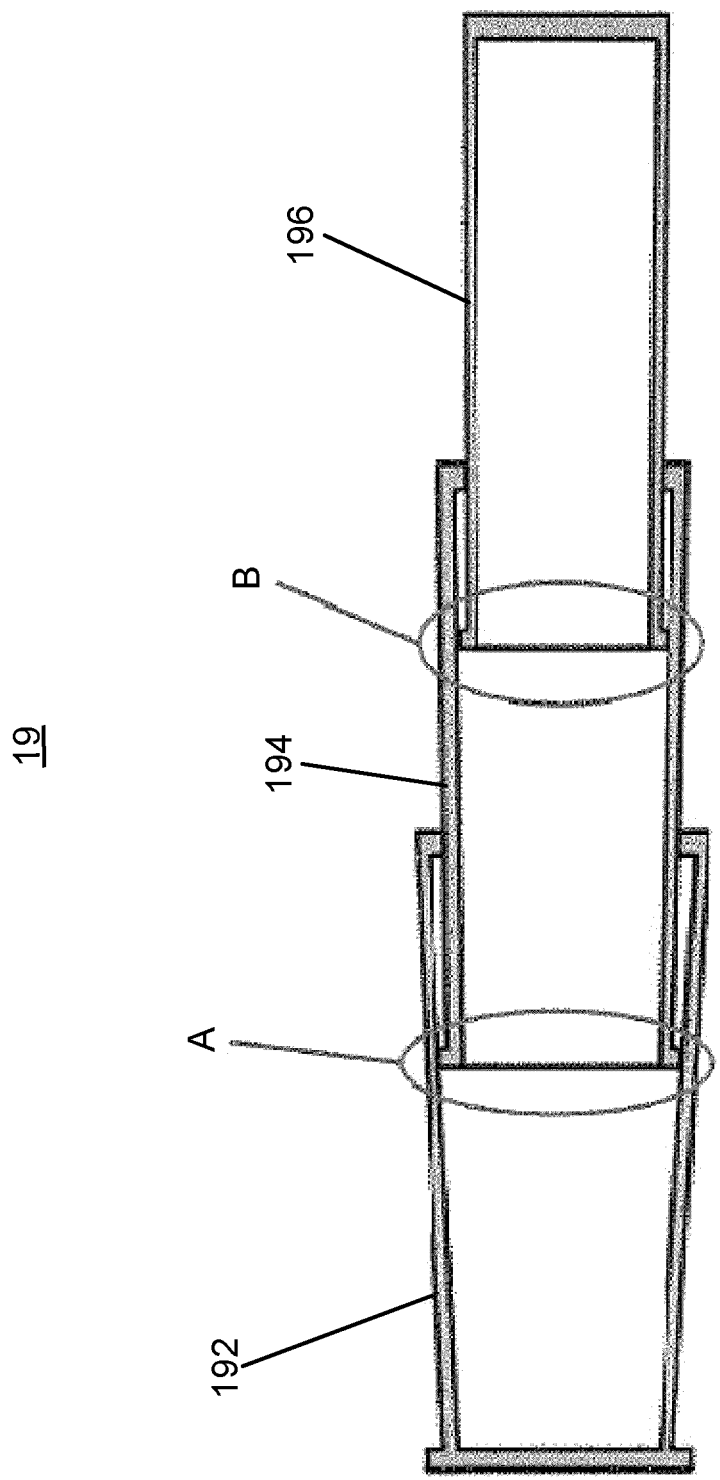
FIG. 5 is a cross-section view of a telescopic frame of the FIGS. 2 to 4 embodiment of the present disclosure.

FIG. 5 is a cross-section view of the telescopic frame of the embodiment illustrated in FIGS. 2 to 4. FIG. 5 shows the telescopic plunger frame comprising the first telescopic plunger part 192, the second telescopic plunger part 194, and the third telescopic plunger part 196. As shown in FIG. 5, the telescopic plunger unit 19 is in the partially extended state.

FIG. 5 also shows a first friction point A and a second friction point B. The friction force profile of friction point A and friction point B is illustrated in the force-distance graph in FIG. 7.

Friction point A is the point of friction between the first telescopic plunger part 192 and the second telescopic plunger part 194. Specifically, friction point A is the point at which the top circumference of the second telescopic plunger part 194 is in contact with the inner surface of the first telescopic plunger part 192. Similarly, friction point B is the point at which the top circumference of the third telescopic plunger part 196 is in contact with the inner surface of the second telescopic plunger part 194.

Since in the present embodiment the first telescopic plunger part 192 has a conical frustum shape, the friction force at friction point A decreases as the second telescopic plunger part 194 moves towards the distal end of the housing 11, due to the increasing inner diameter of the first telescopic plunger part 192 towards the distal end of the housing 11. Similarly, since the second telescopic plunger part 194 has a conical frustum shape, the friction force at friction point B decreases as the third telescopic plunger part 196 moves towards the distal end of the housing 11, due to the increasing inner diameter of the second telescopic plunger part 194 towards the distal end of the housing 11.

Figure 7:
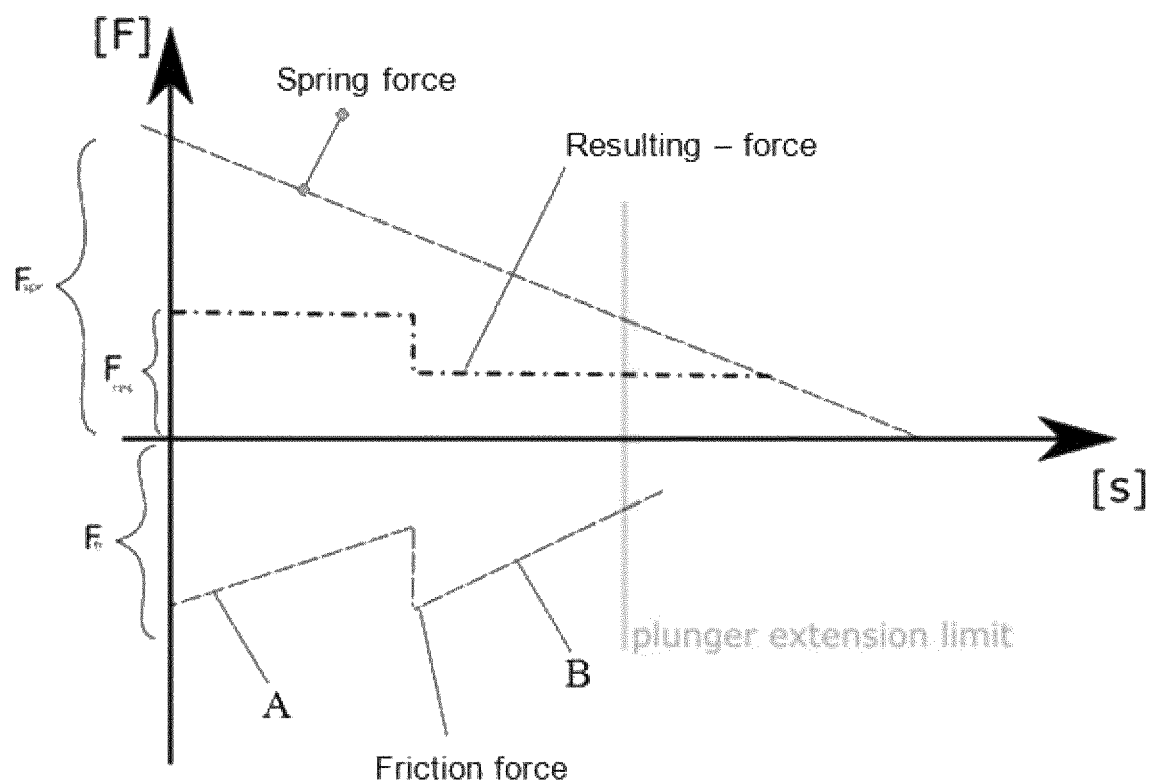
FIG. 7 is a graph illustrating the force profile of a telescopic plunger unit comprising three plunger parts.

The force profile of the friction force between the telescopic plunger parts 192, 194, 196 is represented in the force-distance graph in FIG. 7.

Figure 6:
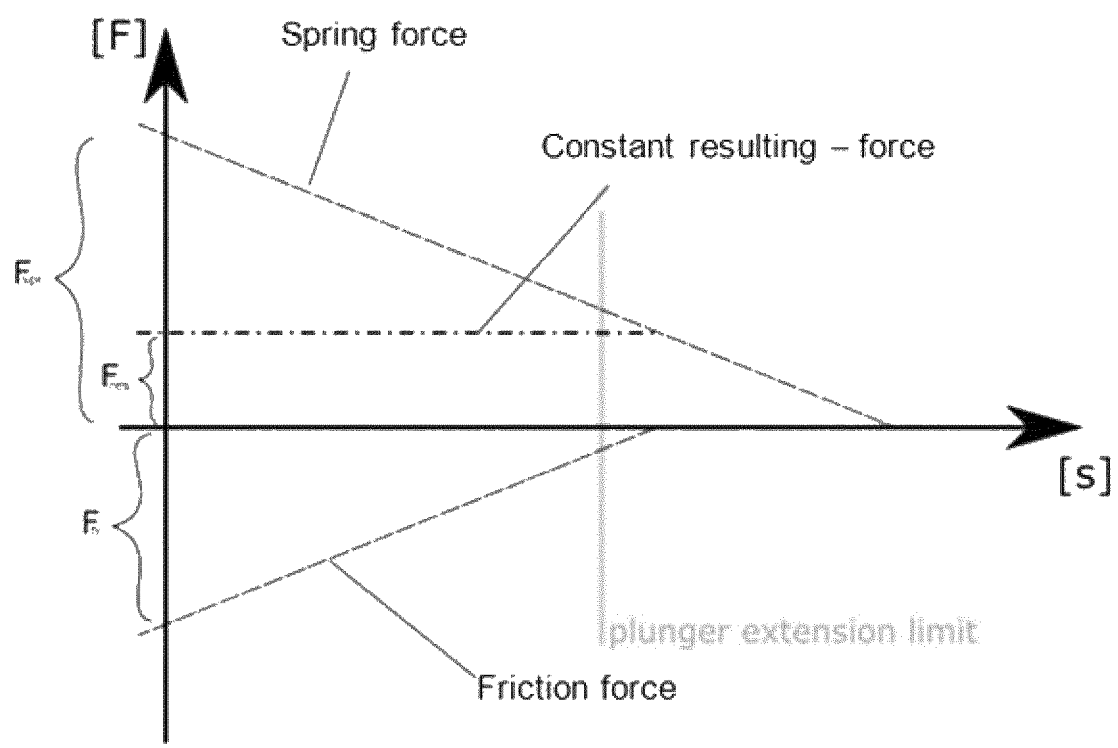
FIG. 6 is a graph illustrating the force profile of a telescopic plunger unit comprising two plunger parts.

FIG. 6 is a graph illustrating the force profile of a telescopic plunger unit comprising two plunger parts. The telescopic plunger unit in this embodiment has a similar configuration of the telescopic plunger unit 19 as shown in FIG. 5, but only with two telescopic plunger parts instead of three.

FIG. 6 is force-distance graph, with force on the x-axis and distance on the y-axis. The spring force (i.e. the force provided by a spring element as the telescopic plunger unit having two telescopic plunger parts extends) and the friction force (i.e. the friction force at a point of contact between the two telescopic plunger parts in the telescopic plunger unit) are represented separately in the force-distance graph. The force-distance graph in FIG. 6 describes the elongation and decompression force of the spring element and the friction force behavior between the two telescopic plunger parts.

The distance [s] is the relative distance between an initial position and a final position of a base the telescopic plunger unit. In other words, the distance [s] is the relative distance of the base between when the telescopic plunger unit is in an initial state (i.e. fully retracted) and when the telescopic plunger unit is in the final state (i.e. fully extended).

As illustrated, the spring force provided by the spring element in this embodiment decreases as the base of the telescopic plunger unit moves from the initial state to the final state. According to Hooke's Law, this is due to the loss of energy stored in the spring element as it is released and begins to decompress.

At the same time, the friction force at the point of contact between the two telescopic plunger parts decreases as the base of the telescopic plunger unit moves from the initial state to the final state. This is due to the increasing inner diameter of the telescopic plunger part. In other words, as the base of the telescopic plunger unit moves towards the distal end of the housing of the auto-injector device, the resistance provided by the inner surface of the telescopic plunger part decreases and therefore the friction force decreases.

When the spring force and the friction force decrease at the same rate (as shown by the same gradient of both force lines in the graph), the resultant force (i.e. [spring force–friction force]) is substantially constant, as demonstrated as $F_{res}$ in the graph. A relatively constant resultant force can also be achieved when the spring force and the friction force decrease at similar rates. In the context of the present disclosure, a "substantially constant" resultant force can be defined as a resultant force having a force profile gradient that is at least 80% less than a force profile gradient of the spring force. Preferably, a "substantially constant" resultant force has a gradient that is 90% less than that of the spring force. It can be clearly seen in FIG. 6 that the gradient of the resultant force is substantially less than that of the spring force.

FIG. 7 is a graph illustrating the force profile of a telescopic plunger unit comprising three plunger parts, as shown in FIGS. 2 to 5.

FIG. 7 is force-distance graph, with force on the x-axis and distance on the y-axis. The spring force (i.e. the force provided by a spring element 25 as the telescopic plunger unit 19 having three telescopic plunger parts 192, 194, 196 extends) and the friction force (i.e. the friction force at points of contact between the three telescopic plunger parts 192, 194, 196 in the telescopic plunger unit 19) are represented separately in the force-distance graph. The force-distance graph in FIG. 7 describes the elongation and decompression force of the spring element and the friction force behavior between the three telescopic plunger parts.

The distance [s] is the relative distance between an initial position and a final position of the base 19a the telescopic plunger unit 19. In other words, the distance [s] is the relative distance of the base 19a between when the telescopic plunger unit 19 is in an initial state (i.e. fully retracted as shown in FIG. 2) and when the telescopic plunger unit is in the final state (i.e. fully extended as shown in FIG. 4).

As illustrated, the spring force provided by the spring element 25 decreases as the base 19a of the telescopic plunger unit 19 moves from the initial state to the final state. According to Hooke's Law, this is due to the loss of energy stored in the spring element 25 as it is released and begins to decompress.

At the same time, the friction force at friction point A decreases (as shown by the first part of the friction force profile) as the telescopic plunger unit 19 extends from the fully retracted state. Specifically, the first part of the friction force profile shows the change in friction force at friction point A as the second telescopic plunger part 194 extends under a pushing force exerted by the spring element 25 as it decompresses. The decreasing friction force is due to the increasing inner diameter of the first telescopic plunger part 192. In other words, as the second telescopic plunger part 194 extends, the resistance provided by the inner surface of the first telescopic plunger part 192 decreases and therefore the friction force decreases.

Due to the existence of more than one friction point in this embodiment, the friction at one point will always be lower than at another point. Therefore, the telescopic plunger parts extends consecutively. In the present embodiment, the friction at friction point A is lower than that at friction point B and therefore the second telescopic plunger part 194 extends before the third telescopic plunger part 196 extends. Once the second telescopic plunger part 194 is fully extended, the third telescopic plunger part 196 begins to extend under the pushing force exerted by the spring element 25 as it decompresses. The friction force at friction point B decreases (as shown by the second part of the friction force profile) as the telescopic plunger unit 19 extends towards the fully extended state. The second part of the friction force profile shows the change in friction force at friction point B as the third telescopic plunger part 196 extends under the pushing force exerted by the spring element 25 as it continues to decompress. The decreasing friction force is due to the increasing inner diameter of the second telescopic plunger part 194. In other words, as the third telescopic plunger part 196 extends, the resistance provided by the inner surface of the second telescopic plunger part 194 decreases and therefore the friction force decreases.

When the spring force and the friction force decrease at the same rate (as shown by the same gradient of the spring force line, the first part of the friction force line (A), and the second part of the friction force line (B) in the graph), the resultant force (i.e. [spring force−friction force]) is substantially constant (i.e. having a gradient that is at least 80% less than that of the spring force) as the second telescopic plunger part 194 extends and is also substantially constant (but at a lower value) as the third telescopic plunger part 196 extends. This is illustrated as $F_{res}$ in the graph having a step. A relatively constant resultant force can also be achieved when the spring force and the friction force decrease at similar rates.

In alternative embodiments, the telescopic frame may comprise a different number of telescopic plunger parts. For example, a telescopic frame in such alternative embodiments may have only two telescopic plunger parts so as to be accommodated in a smaller-sized auto-injector. The number of telescopic plunger parts in a telescopic frame may depend on dimensions of the auto-injector, the size and force provided by the spring element and other considerations such as those associated with the movement of the telescopic plunger unit.

In alternative embodiments, the telescopic frame may be made of other compressible materials such as rubber, so as to achieve the same affect that friction is provided throughout the extension of the telescopic plunger unit.

In alternative embodiments, instead of having a conical frustum shape, the telescopic plunger parts of the telescopic frame may adopt different shape that also achieve the effect of decreasing friction between telescopic plunger parts. For example, in such alternative embodiments the first telescopic plunger part may have a cylindrical shape and a tapered inner surface such that friction between the first and second telescopic plunger parts decreases as the telescopic plunger unit extends under driving force from the spring element.

In alternative embodiments, instead of a rod, the plunger element may be formed in a different shape.

In alternative embodiments, instead of a hook and a slot, the first and second locking elements may adopt a different configuration. For example, in an alternative embodiment the locking mechanism may comprise a groove at the plunger element as the first locking element, and a movable projection as the second locking element. In this alternative embodiment when the projection is in a first position it is engaged with the groove so as to hold the spring element in the initial compressed state, and when the projection is in a second position it is disengaged from the groove such that the spring element is released and begins to decompress.

In alternative embodiments, instead of a T-shape, the hook of the locking mechanism may adopt another shape, such as an L-shape so as to engage the slot provided at the plunger element of the telescopic plunger unit.

In alternative embodiments, instead of rubber, the rotatable cap may be made of other high friction materials that allow easy gripping and rotation of the cap.

Although it has been described in the above that the second orientation is achieved by rotating the rotatable cap by 90° from the first orientation, in alternative embodiments the first and second orientations may be separated by a different angle.

In alternative embodiments, instead of a rotatable cap, an activation mechanism may be provided at the proximal end of the housing of the auto-injector, wherein a hook is fixed to the activation mechanism and upon activating the activation mechanism the hook is configured to disengage from the slot at the plunger element. In such embodiments, the activation mechanism may be a button provided at the proximal end of the housing for manual operation.

Although claims have been formulated in this application to particular combinations of features, it should be understood that the scope of the disclosure also includes any novel features or any novel combinations of features disclosed herein either explicitly or implicitly or any generalisation thereof The applicant hereby gives notice that new claims may be formulated to such features and/or combinations of features during the prosecution of the present application or of any further application derived therefrom.

Although a few embodiments have been shown and described, it would be appreciated by those skilled in the art that changes may be made in these embodiments without departing from the principles of the disclosure.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoylgamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An auto-injector configured to deliver a liquid medicament, the auto-injector comprising:
   a housing arranged to contain a syringe, the housing comprising a piston configured to seal the syringe and displace the medicament, the housing having a proximal end and a distal end, wherein the distal end is configured to be applied against an injection site; and
   a telescopic plunger unit arranged between the piston and the distal end of the housing, the telescopic plunger unit comprising a telescopic frame and a spring element surrounding a plunger element, wherein the plunger element is fixed to a base of the telescopic plunger unit and the spring element is configured to be held in an initial compressed state by a compressive force exerted by the base of the telescopic plunger unit,
   wherein, when the spring element is released, a tapering profile of the telescopic frame is configured to provide varying friction with extension such that resistance to telescopic extension decreases as spring force provided by the spring element decreases with increasing extension of the telescopic plunger unit, and
   wherein a combination of the decreasing spring force provided by the spring element and the decreasing resistance to telescopic extension provides a substantially constant resultant driving force exerted on the base of the telescopic plunger unit, such that a substantially constant pushing force is exerted on the piston when the spring element is released.

2. The auto-injector of claim 1, wherein the substantially constant resultant driving force has a force profile gradient of at least 80% less than that of a gradient of the decreasing spring force.

3. The auto-injector of claim 1, wherein the telescopic frame comprises a plurality of telescopic plunger parts, and each of the plurality of telescopic plunger parts has a conical frustum shape.

4. The auto-injector of claim 3, wherein the plurality of telescopic plunger parts comprises an outermost telescopic plunger part, and the outermost telescopic plunger part is configured to be fixedly attached to the proximal end of the housing.

5. The auto-injector of claim 1, further comprising a locking mechanism arranged at the proximal end of the housing, the locking mechanism being configured such that when the locking mechanism is disengaged, the spring element releases and exerts a driving force on the base of the telescopic plunger unit, thereby forwarding a load of the spring element to the plunger element and extending the telescopic plunger unit, pushing the piston towards the distal end of the housing to displace the medicament.

6. The auto-injector of claim 5, wherein the locking mechanism comprises a first locking element provided at the plunger element, and a second locking element, the first and second locking elements being configured to be releasably engaged with each other.

7. The auto-injector of claim 6, wherein the first locking element is a groove provided at the plunger element, and the second locking element is a movable projection, wherein, when the moveable projection is in a first position, the moveable projection is engaged with the groove to hold the spring element in the initial compressed state, and wherein, when the projection is in a second position, the moveable projection is disengaged from the groove such that the spring element is released.

8. The auto-injector of claim 6, wherein the first locking element is a slot provided at the plunger element, and the second locking element is a hook provided at a rotatable cap at the proximal end of the housing, wherein, when the hook is in a first orientation, the hook is engaged with the slot to hold the spring element in the initial compressed state, and wherein, when the hook is in a second orientation, the hook is disengaged from the slot such that the spring element is released.

9. The auto-injector of claim 8, wherein the second orientation is achieved by rotating the rotatable cap from the first orientation.

10. The auto-injector of claim 8, wherein knurls are provided on an outer edge of the rotatable cap.

11. The auto-injector of claim 1, further comprising a medicament included in the syringe.

12. A method of maintaining a substantially constant resultant driving force in an auto-injector, the method comprising:
providing an auto-injector comprising a telescopic plunger unit and a spring element,
wherein a tapering profile of a telescopic frame of the telescopic plunger unit is configured to provide varying friction with extension such that resistance to telescopic extension decreases as spring force provided by the spring element decreases with increasing extension of the telescopic plunger unit, and a combination of the decreasing spring force provided by the spring element and the decreasing resistance to telescopic extension provides the substantially constant resultant driving force exerted on a base of the telescopic plunger unit.

* * * * *

UNITED STATES PATENT AND TRADEMARK OFFICE
CERTIFICATE OF CORRECTION

PATENT NO. : 10,653,844 B2
APPLICATION NO. : 15/778349
DATED : May 19, 2020
INVENTOR(S) : Stefan Wendland and Michael Harms Page 1 of 1

It is certified that error appears in the above-identified patent and that said Letters Patent is hereby corrected as shown below:

In the Specification

Column 1, Line 9, after "filed", delete "in"

Signed and Sealed this
Eleventh Day of August, 2020

Andrei Iancu
*Director of the United States Patent and Trademark Office*